(12) United States Patent
Suelmann

(10) Patent No.: US 10,448,592 B2
(45) Date of Patent: Oct. 22, 2019

(54) CUCUMBER VARIETY NUN 52010 CUP

(71) Applicant: Nunhems B.V., AB Nunhem (NL)

(72) Inventor: Johannes Josephus Suelmann, Roermond (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 15/898,733

(22) Filed: Feb. 19, 2018

(65) Prior Publication Data

US 2018/0184605 A1   Jul. 5, 2018

Related U.S. Application Data

(60) Provisional application No. 62/474,223, filed on Mar. 21, 2017.

(51) Int. Cl.
*A01H 5/08* (2018.01)
*A01H 6/34* (2018.01)
*A01H 5/10* (2018.01)

(52) U.S. Cl.
CPC ............ *A01H 5/10* (2013.01); *A01H 5/08* (2013.01); *A01H 6/346* (2018.05)

(58) Field of Classification Search
None
See application file for complete search history.

(56) References Cited

U.S. PATENT DOCUMENTS

| | | | |
|---|---|---|---|
| 4,822,949 | A | 4/1989 | Niego et al. |
| 5,349,128 | A | 9/1994 | Quemada et al. |
| 5,492,827 | A | 2/1996 | Dirks |
| 6,084,152 | A | 7/2000 | Kwak et al. |
| 6,765,130 | B2 | 7/2004 | Taurick |
| 9,167,761 | B2 | 10/2015 | Shetty |
| 2014/0317769 | A1 | 10/2014 | Suelmann |
| 2014/0356514 | A1 | 12/2014 | Suelmann |
| 2015/0181824 | A1 | 7/2015 | Suelmann |
| 2017/0127631 | A1 | 5/2017 | Shetty |

FOREIGN PATENT DOCUMENTS

| | | |
|---|---|---|
| WO | 2013182646 A1 | 12/2013 |
| WO | 2014076249 A1 | 5/2014 |
| WO | 2016120438 A1 | 8/2016 |
| WO | 2016207432 A1 | 12/2016 |

OTHER PUBLICATIONS

Colijn-Hooymans, C.M., et al., Competence for regeneration of cucumber cotyledons is restricted to specific developmental stages, Plant Cell, Tissue and Organ Culture, 1994, pp. 211-217, vol. 39.
Martin, Eugenia, et al., Identification of markers linked to agronomic traits in globe artichoke, Australian Journal of Crop Science, 2008, pp. 43-46, vol. 1, No. 2.
Nikolovai, Vesselina, et al., Diploidization of Cucumber (*Cucumis Sativus* L.) Haploids by Colchicine Treatment, Acta Societatis Botanicorum Poloniae, 1996, pp. 311-317, vol. 65, No. 3-4.
Sarreb, D.A., et al., Comparison of triploid and diploid cucumber in long-term liquid cultures, Plant Cell Tissue, Organ Culture, 2002, pp. 231-235, vol. 71.
Vos, Pieter, et al., AFLP: a new technique for DNA fingerprinting, Nucleic Acids Research, 1995, pp. 4407-4414, vol. 23 No. 21.
Sang-Gu, Kim, et al., Callus growth and plant regeneration in diverse cultivars of cucumber (*Cucumis sativus* L.), Plant Cell, Tissue and Organ Culture, 1988, pp. 67-74, vol. 12.
Wijnker, Erik, et al., Hybrid recreation by reverse breeding in *Arabidopsis thaliana*, Nature Protocols, 2014, pp. 761-772, vol. 9.
Pisanu, A.B., et al., Yield and Biometric Characteristics of 9 Clones Selected from the Population of "Spinoso sardo" Artichokes, Acta Hort., 660, ISHS 2004.
Parvathaneni, Rajiv Krishna, et al., Fingerprinting in Cucumber and Melon (*Cucumis* spp.) Genotypes Using Morphological and ISSR Markers, J. Crop Sci. Biotech., 2011, pp. 39-43, vol. 14, No. 1.
Guidelines for the Conduct of Tests for Distinctness, Uniformity and Stability, TG/61/7 (Geneva 2007, last revised 2016), as published by UPOVhttp://www.upov.int/en/publications/tg-rom/tg061/tg_61_7.pdf.
Objective Description of Variety—Cucumber (*Cucumis sativus* L.) as published by the US Department of Agriculture, Agricultural Marketing Service, Plant Variety Protection Office, Beltsville, MD 20705https://www.ams.usda.gov/sites/default/files/media/93-Cucumber%20ST-470-93%202015.pdf, Jun. 2015.
Weng et al, 2015, Theor. Appl. Genet. 128: 1747-1763.

*Primary Examiner* — Brent T Page
(74) *Attorney, Agent, or Firm* — Arent Fox LLP

(57) ABSTRACT

The invention provides a new and distinct hybrid variety of Cucumber, NUN 52010 CUP as well as seeds and plants and fruits thereof.

24 Claims, No Drawings

CUCUMBER VARIETY NUN 52010 CUP

CROSS-REFERENCE TO RELATED APPLICATIONS

The present application claims the benefit of U.S. Patent Application Ser. No. 62/474,223, filed 21 Mar. 2017, which is incorporated herein by reference in its entirety.

FIELD OF THE INVENTION

The present invention relates to the field of plant breeding and, more specifically, to the development of NUN 52010 CUP (also designated as NUN 52010 or NUN 52010 F1 or NUN 52010 hybrid). The invention further relates to vegetative reproductions of NUN 52010 CUP, methods for tissue culture of NUN 52010 CUP and regenerating a plant from such a tissue culture and also to phenotypic variants of NUN 52010 CUP.

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential. One crop species which has been subject to such breeding programs and is of particular value is the Cucumber.

Cucumber (*Cucumis sativus* L.) is naturally a diploid (2n=14) outcrossing species, although haploid, doubled-haploid (see, e.g., U.S. Pat. No. 5,492,827), and triploid (see, e.g., Sarreb et al. (2002), Plant Cell Tissue, Organ Culture 71: 231-235) types have been developed. The two main types of cucumber fruit grown commercially today in the United States are fresh market (slicing) type and the processing (pickling) type. Varieties and production methods are typically adapted to the end use. Slicing cucumbers are often longer, larger and have darker and thicker skin, whereas pickling/processing cucumbers have a shorter fruit, thinner skin with interior flesh that make them more amenable to pickling. Seedless varieties are generally preferable for both fresh market and for pickling as seeds are not palatable.

Cucumber plants that set fruit parthenocarpically (without pollination and fertilization) have more recently been available. These plants produce seedless fruit unless pollinated. Growth of parthenocarpic varieties is beneficial in that setting of fruit on these cultivars does not produce an inhibiting effect on plant growth, unlike the case of fertilized, seeded fruit. The seedless varieties are usually higher yielding and of higher quality due to the lack of seeds. However, growth of these plants requires isolation from seeded cucumbers to avoid pollination and subsequent seeded fruit.

Most of the cucumbers currently grown for processing to pickles and pickle products in the United States are seeded hybrid varieties. Hybrid varieties offer the advantages of easy combination of dominant and recessive traits, such as disease resistance, from a set of inbred parents, as well as careful control of parentage. The production of F1 hybrid cucumber seeds from a pollen parent bearing only male flowers has been reported (see, e.g., U.S. Pat. No. 4,822,949).

Many different cucumber cultivars have been produced, and cucumber breeding efforts have been underway in many parts of the world (see e.g. U.S. Pat. No. 6,765,130). Some breeding objectives include varying the color, texture and flavor of the fruit. Minimizing the occurrence of bitterness in cucumbers is one such example. Other objectives include optimizing flesh thickness, solid content (% dry matter), and sugar content. Also, breeding programs have focused on developing plants with earlier fruit maturity; more restricted vine growth, improved disease resistance or tolerance, and improved adaptability to environmental conditions.

Advances in biotechnology have also resulted in genetically engineered cucumber plants with improved traits. For example, cucumbers resistant to CMV have been developed by expression of CMV protein coat genes (see e.g. U.S. Pat. No. 5,349,128). Transgenic plants exhibiting, for example, other viral resistance traits or high levels of superoxide dismutase have also been reported (see e.g. U.S. Pat. No. 6,084,152).

While breeding efforts to date have provided a number of useful cucumber varieties with beneficial traits, there remains a great need in the art for new varieties with further improved traits. Such plants would benefit farmers and consumers alike by improving crop yields and/or quality. Some breeding objectives include varying the color, texture and flavor of the fruit, and absence of seeds. Other objectives include disease or pest resistance, optimizing flesh thickness, yield, suitability to various climatic circumstances, solid content (% dry matter), and storage properties.

SUMMARY OF THE INVENTION

In an aspect of the invention, a seed of Cucumber variety NUN 52010 CUP is provided, wherein a representative sample of said seed will be deposited under Accession Number NCIMB 43415. The invention also provides for a plurality of seeds of NUN 52010 CUP. The Cucumber seed of NUN 52010 CUP may be provided as an essentially homogeneous population of Cucumber seed. Therefore, seed of the invention may be defined as forming at least about 97% of the total seed, including at least about 98%, 99% or more of the seed. The population of seed of NUN 52010 CUP may be particularly defined as being essentially free from other seed. The seed population may be grown into plants to provide an essentially homogeneous population of Cucumber plants according to the invention.

Also encompassed is a plant grown from a seed of Cucumber variety NUN 52010 CUP and a plant part thereof. In another aspect the invention provides for a hybrid variety of Cucumber called NUN 52010 CUP. The invention also provides for a progeny of NUN 52010 CUP. Especially, a plant or a progeny retaining all or all but one, two or three of the "distinguishing characteristics" or all or all but one, two or three of the "morphological and physiological characteristics" of NUN 52010 CUP referred to herein, is encompassed herein as well as methods for producing that plant or progeny.

In one aspect, a plant or a progeny of the invention have all the physiological and morphological characteristics of variety NUN 52010 CUP when grown under the same environmental conditions. In another aspect such a plant or such progeny have all or all but one, two or three of the physiological and morphological characteristics of NUN 52010 CUP when measured under the same environmental conditions and evaluated at significance levels of 1%, 5% or 10% significance (which can also be expressed as a p-value) wherein a representative sample of seed of variety NUN 52010 CUP will be deposited under Accession Number NCIMB 43415. In a second aspect, a plant or a progeny of the invention have all the physiological and morphological characteristics of variety NUN 52010 CUP when grown under the same environmental conditions. In another aspect such a plant or such progeny have all or all but one, two or three of the physiological and morphological characteristics as listed in Table 1 and/or 2 for variety NUN 52010 CUP when measured under the same environmental conditions and evaluated at significance levels of 1%, 5% or 10% significance.

In another aspect a plant of NUN 52010 CUP or said progeny plants has 7, 8, or more or all of the distinguishing characteristics: 1) Average fruit diameter at medial at harvest maturity; 2) Spine density type at edible maturity; 3) Type of stem end cross section at edible maturity; 4) Type of blossom end cross section at edible maturity; 5) Average leaf petiole length; 6) Average leaf length; 7) Average leaf width; 8) Average number of nodes form Cotyledon leaves to node bearing the first pistillate flower; and 9) Average leaf petiole diameter. NUN 52010 CUP is a pickling cucumber for hand harvest and is parthenocarpic.

Also a plant part obtained from variety NUN 52010 CUP is provided, wherein said plant part is selected from the group consisting of: a fruit, a harvested fruit, a part of a fruit, a seedless fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof. Fruits are particularly important plant parts. In a further embodiment, the plant part obtained from variety NUN 52010 CUP is a cell, optionally a cell in a cell or tissue culture. That cell may be grown into a plant of NUN 52010 CUP.

The invention also provides a cell culture of NUN 52010 CUP and a plant regenerated from NUN 52010 CUP, which plant has all the characteristics of NUN 52010 CUP when grown under the same environmental conditions, as well as methods for regenerating NUN 52010 CUP. Alternatively, a regenerated plant may have one characteristic that is different from NUN 52010 CUP.

Further, a vegetatively propagated plant of variety NUN 52010 CUP is provided having all or all but one, two or three of the morphological and physiological characteristics NUN 52010 CUP when grown under the same environmental conditions.

Also, a Cucumber fruit produced on a plant grown from a seed of NUN 52010 CUP is provided.

In still another aspect, a seed growing or grown on a plant of NUN 52010 CUP is provided (i.e. produced after pollination of the flower of NUN 52010 CUP).

Definitions

All patent and non-patent documents cited herein are incorporated by reference in their entirety "Cucumber" refers herein to plants of the species *Cucumis sativus*. The most commonly eaten part of a Cucumber is the fruit or pepo.

"Cultivated Cucumber" refers to plants of *Cucumis sativus* i.e. varieties, breeding lines or cultivars of the species *C. sativus*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of Cucumber.

"Pickling Cucumber" refers to Cucumbers suitable for processing by pickling in brine, vinegar, marinade or other solution. Said processing includes allowing the Cucumbers to ferment for a period of time by immersion in an acidic liquid or though lacto-fermentation. Pickled pickling Cucumbers are also known as pickles or gherkins.

The terms "Cucumber plant designated NUN 52010 CUP", "NUN 52010 CUP", "NUN 52010", "NUN 52010 F1", "52010 CUP" or "Cucumber 52010" are used interchangeably herein and refer to a Cucumber plant of variety NUN 52010 CUP, representative seed of which will be deposited under Accession Number NCIMB 43415.

A "seed of NUN 52010 CUP" refers to a Cucumber seed which can be grown into a plant of NUN 52010 CUP wherein a representative sample of viable seed of NUN 52010 CUP will be deposited under Accession Number NCIMB 43415. A seed can be in any stage of maturity, for example a mature, viable seed, or an immature, non-viable seed. A seed comprises an embryo and maternal tissues.

An "embryo of NUN 52010 CUP" refers to an "F1 hybrid embryo" as present in a seed of NUN 52010 CUP, a representative sample of said seed of NUN 52010 CUP will be deposited under Accession Number NCIMB 43415.

A "seed grown on NUN 52010 CUP" refers to a seed grown on a pollinated mature plant of NUN 52010 CUP or inside a pollinated fruit of NUN 52010 CUP. The "seed grown on NUN 52010 CUP" contains tissues and DNA of the maternal parent, NUN 52010 CUP. The "seed grown on NUN 52010 CUP" contains an F2 embryo. When said seed is planted, it grows into a first generation progeny plant of NUN 52010 CUP.

A "fruit of NUN 52010 CUP" refers to a fruit containing maternal tissues of NUN 52010 CUP as deposited under Accession Number NCIMB. NUN 52010 CUP sets fruit parthenocarpically, such fruit does not contain seed. The skilled person is familiar with methods for inducing parthenocarpy. Those methods comprise chemically or genetically inducing parthenocarpy. Compounds suitable for chemically inducing parthenocarpy include auxins, gibberellins and cytokinins. Genetic parthenocarpy can a.o. be induced as in WO2016207432 or WO2016120438 (PIN4) or can be provided by reduced or eliminated expression of PISTILATA (PI) or APETALA3 (AP3). A fruit can be in any stage of maturity, for example a mature fruit in the yellow stage, or an immature fruit in the edible green stage. Pollinated fruit contains seed. The fruit comprises a stem and peduncle or pedicel, receptacle, ectocarp, rind, fruit flesh, exocarp, mesocarp, external phloem, internal phloem, xylem, vascular bundle, carpel, placenta and optionally seed. The stem and peduncle or pedicel, receptacle, ectocarp, rind, fruit flesh, exocarp, mesocarp, external phloem, internal phloem, xylem, vascular bundle, carpel, placenta and seed coat of the seed are maternal tissues, so they are genetically identical to the plant on which they grow.

"Tissue culture" or "cell culture" refers to a composition comprising isolated cells of the same or a different type or a collection of such cells organized into parts of a plant. Tissue culture of various tissues of cucumber and regeneration of plants therefrom is well known and widely published (see, e.g., Sang-Gu et al. (1988), Plant Cell, Tissue and Organ Culture 12: 67-74; Colijn-Hooymans (1994), Plant Cell, Tissue and Organ Culture 39: 211-217). Similarly, the skilled person is well-aware how to prepare a "tissue culture" or "cell culture".

"UPOV descriptors" are the plant variety descriptors described for cucumber in the "Guidelines for the Conduct of Tests for Distinctness, Uniformity and Stability, TG/61/7 (Geneva 2007, last revised 2016), as published by UPOV (International Union for the Protection of New Varieties and Plants, available on the world wide web at upov.int) and which can be downloaded from the world wide web at upov.int/ under edocs/tgdocs/en/tg061.pdf and is herein incorporated by reference in its entirety.

"USDA descriptors" are the plant variety descriptors for cucumber as described in the document titled "OBJECTIVE DESCRIPTION OF VARIETY—Cucumber (*Cucumis sativus* L.)" as published by the US Department of Agriculture, Agricultural Marketing Service, Plant Variety Protection Office, Beltsville, Md. 20705 and which can be downloaded from the World Wide Web at ams.usda.gov/ under sites/default/files/media/93-Cucumber.pdf. "Non-USDA descriptors" are other descriptors suitable for describing cucumber.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007 (The Royal Horticultural Society, charity No: 222879, PO Box 313 London SW1P2PE.

As used herein and except as otherwise indicated, the term "plant" includes the whole plant or any part thereof, preferably having the same genetic makeup as the plant from which it is obtained, such as a plant organ (e.g. harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or parts of a plant (e.g. harvested tissues or organs), such as a fruit, a harvested fruit, a part of a fruit, a seedless fruit, a leaf, a part of a leaf, pollen, an ovule, an embryo, a petiole, a shoot or a part thereof, a stem or a part thereof, a root or a part thereof, a root tip, a cutting, a seed, a part of a seed, seed coat or another maternal tissue which is part of a seed grown on a variety of the invention, hypocotyl, cotyledon, a scion, a graft, a stock, a rootstock, a pistil, an anther, and a flower or parts of any of these and the like. Also any developmental stage is included, such as seedlings, cuttings prior or after rooting, mature plants or leaves. Alternatively, a plant part may also include a plant seed which comprises one or two sets of chromosomes derived from the parent plant, e.g. from NUN 52010 CUP. An F2 progeny produced from self-pollination of NUN 52010 CUP will thus comprise two sets of chromosomes derived from NUN 52010 CUP, while an F2 progeny derived from cross-fertilization of NUN 52010 CUP will comprise only one set of chromosomes from NUN 52010 CUP and the other set of chromosomes from the other parent.

"Harvested plant material" refers herein to plant parts (e.g. fruits detached from the whole plant) which have been collected for further storage and/or further use.

"Reference Variety" or "check variety" refers herein to variety Gershwin (or Gershwin RZ), a commercial variety from company Rijk Zwaan, which has been planted in a trial together with NUN 52010 CUP. Thus, USDA descriptors of NUN 52010 were compared to the USDA descriptors of Gershwin.

"Rootstock" or "stock" refers to the plant selected for its roots, in particular for the resistance of the roots to diseases or stress (e.g. heat, cold, salinity etc.). Normally the quality of the fruit of the plant providing the rootstock is less important.

"Scion" refers to a part of the plant that is attached to the rootstock. This plant is selected for its stems, leaves, flowers, or fruits. The scion contains the desired genes to be duplicated in future production by the stock/scion plant and may produce the desired Cucumber fruit.

"Stock/scion" or grafted plant refers to a Cucumber plant comprising a rootstock from one plant grafted to a scion from another plant.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g. the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 or "all or all but one, two or three of the physiological and morphological characteristics" of Table 1 and/or 2.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of NUN 52010 CUP may have one or more (or all) of the essential physiological and/or morphological characteristics of said variety listed in Table 1 and/or 2, as determined at the 5% significance level (i.e. p<0.05) when grown under the same environmental conditions.

"Distinguishing characteristics" or "distinguishing morphological and/or physiological characteristics" refers herein to the characteristics which distinguish (i.e. are different) between the new variety and other Cucumber varieties, such as the Reference Variety, when grown under the same environmental conditions. The distinguishing characteristics between NUN 52010 CUP and Reference Variety are described elsewhere herein and also can be seen in Table 1 and/or Table 2. When comparing NUN 52010 CUP with different varieties, the distinguishing characteristics will be different. In one aspect, the distinguishing characteristics may therefore include at least one, two, three or more (or all) of the characteristics listed in Table 1 and/or 2 and/or 3. All numerical distinguishing characteristics are statistically significantly different at p<0.05 between NUN 52010 CUP and the other variety, e.g. Reference Variety.

NUN 52010 CUP has the following distinguishing characteristics when compared to the Reference Variety: 1) Average fruit diameter at medial at harvest maturity; 2) Spine density type at edible maturity; 3) Type of stem end cross section at edible maturity; 4) Type of blossom end cross section at edible maturity; 5) Average leaf petiole length; 6) Average leaf length; 7) Average leaf width; 8) Average number of nodes form Cotyledon leaves to node bearing the first pistillate flower; and 9) Average leaf petiole diameter. This can be seen in Table 1, where the USDA characteristics of NUN 52010 CUP are compared to the characteristics of Reference Variety, when grown under the same environmental conditions Thus, a Cucumber plant "comprising the distinguishing characteristics of NUN 52010 CUP (such as a progeny plant) refers herein to a plant which does not differ significantly from said variety in the distinguishing characteristics above. Therefore in one aspect a plant (such as a progeny plant of NUN 52010 CUP) is provided which does not differ significantly from NUN 52010 CUP in the distinguishing characteristics above.

Similarity and differences between two different plant lines or varieties can be determined by comparing the number of morphological and/or physiological characteristics (e.g. the characteristics as listed in Table 1 and/or 2) that are the same (i.e. statistically not significantly different) or that are different (i.e. statistically significantly different) between the two plant lines or varieties when grown under the same environmental conditions. A numerical characteristic is considered to be "the same" when the value for a numeric characteristic is not significantly different at the 1% ($p<0.01$) or 5% ($p<0.05$) significance level, using one way Analysis of variance (ANOVA), a standard method known to the skilled person. Non-numerical or "degree" or "type" characteristic are considered "the same" when the values have the same "degree" or "type" when scored using USDA and/or UPOV descriptors, if the plants are grown under the same environmental conditions.

As used herein, the term "variety", "cultivated Cucumber" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A "plant line" is for example a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Yield" means the total weight of all Cucumber fruits harvested per hectare of a particular line or variety. It is understood that "yield" expressed as weight of all Cucumber fruits harvested per hectare can be obtained by multiplying the number of plants per hectare times the "yield per plant". "Marketable yield" means the total weight of all marketable Cucumber fruits, especially fruit that is not cracked, damaged or diseased, harvested per hectare of a particular line or variety.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

"Harvest maturity" is referred to as the stage at which a Cucumber fruit is ripe or ready for harvest or the optimal time to harvest the fruit for the market, for processing or for consumption. In one embodiment, harvest maturity is the stage which allows proper completion of the normal ripening.

The term "traditional breeding techniques" encompasses herein crossing, selfing, selection, doubled haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one Cucumber line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 52010 CUP. A progeny may be obtained by regeneration of cell culture or tissue culture or parts of a plant of said variety or selfing of a plant of said variety or by producing seeds of a plant of said variety. In further embodiments, progeny may also encompass plants obtained from crossing of at least one plant of said variety with another Cucumber plant of the same variety or another variety or (breeding) line, or with wild Cucumber plants. A progeny may comprise a mutation or a transgene. A first generation progeny" or is the progeny directly derived from, obtained from, obtainable from or derivable from the parent plant by, e.g., traditional breeding methods (selfing and/or cross-pollinating) or regeneration. Thus, a plant of NUN 52010 CUP is the male parent, the female parent or both of a first generation progeny of NUN 52010 CUP. Progeny may have all the physiological and morphological characteristics of variety NUN 52010 CUP when grown under the same environmental conditions and/or progeny may have (be selected for having) one or more of the distinguishing characteristics of Cucumber of the invention. Using common breeding methods such as backcrossing or recurrent selection, one or more specific characteristics may be introduced into said variety, to provide or a plant comprising all but 1, 2, or 3 or more of the morphological and physiological characteristics of NUN 52010 CUP (as listed in Table 1 and/or 2)

The terms "gene converted" or "conversion plant" or "single locus converted plant" in this context refer to Cucumber plants which are developed by backcrossing wherein essentially all of the desired morphological and physiological characteristics of the parent variety or line are recovered, in addition to the one or more genes transferred into the parent via the backcrossing technique (optionally including reverse breeding or reverse synthesis of breeding lines) or via genetic engineering or through mutation breeding. Likewise a "Single Locus Converted (Conversion) Plant" refers to plants which are developed by plant breeding techniques comprising or consisting of mutation and/or by genetic transformation and/or by backcrossing, wherein essentially all of the desired morphological and physiological characteristics of a Cucumber variety are recovered in addition to the characteristics of the single locus having been transferred into the variety via the backcrossing technique. In case of a hybrid, the gene may be introduced in the male or female parental line.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for Cucumbers described herein. The mean, if not indicated otherwise within this application, refers to the arithmetic mean of measurements on at least 10 different, randomly selected plants of a variety or line.

DETAILED DESCRIPTION

The present invention relates to a plant of NUN 52010 CUP wherein a representative sample of seeds of said variety will be deposited under the Budapest Treaty, with Accession number NCIMB 43415.

The present invention also relates to a seed of Cucumber variety, referred to as NUN 52010 CUP, wherein a representative sample of said seed is deposited under the Budapest Treaty, with Accession number NCIMB 43415.

In another aspect, the invention provides for a Cucumber plant part of variety NUN 52010 CUP, preferably a fruit, a representative sample of seed from said variety will be deposited under the Budapest Treaty, with Accession number NCIMB 43415.

A seed of hybrid variety NUN 52010 CUP is obtainable by crossing the male parent of said variety with the female parent of said variety and harvesting the seeds produced on the female parent. The resultant seeds of said variety can be grown to produce plants of said variety. In one embodiment a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of NUN 52010 CUP.

Also provided is a plant of Cucumber variety NUN 52010 CUP, or a fruit or other plant part thereof, produced from a seed, wherein a representative sample of said seeds will be deposited under the Budapest Treaty, with Accession Number NCIMB 43415.

Also a plant part obtained from variety NUN 52010 CUP is provided, wherein said plant part is selected from the group consisting of: a fruit, a harvested fruit, a part of a fruit, a seedless fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof. Fruits are particularly important plant parts. Fruits may be parthenocarpic or seedless (optionally induced with auxins, gibberellins and cytokinins), or contain immature and/or nonviable seeds, or contain viable seed. In a further embodiment, the plant part obtained from variety NUN 52010 CUP is a cell, optionally a cell in a cell or tissue culture. That cell may be grown into a plant of NUN 52010 CUP. A part of a variety of the invention, i.e. NUN 52010 CUP (or of progeny NUN 52010 CUP or of a plant having all physiological and/or morphological characteristics but one, two or three which are different from those of NUN 52010 CUP) further encompasses any cells, tissues, organs obtainable from the seedlings or plants in any stage of maturity.

The invention also provides for a food or feed product or a processed product comprising or consisting of a plant part described herein wherein the plant part can be identified as a part of the plant of the invention. Preferably, the plant part is a Cucumber fruit or part thereof and/or an extract from a fruit or another plant part described herein comprising at least one cell of NUN 52010 CUP. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Such a plant part of NUN 52010 CUP can be stored and/or processed further. Encompassed are therefore also food or feed products comprising one or more of such parts, such as canned, chopped, cooked, roasted, in a sauce, in a sandwich, pasted, puréed or concentrated, juiced, frozen, dried, pickled, or powdered Cucumber fruit from NUN 52010 CUP or from progeny of said varieties, or from a derived variety, such as a plant having all but one, two or three physiological and/or morphological characteristics of NUN 52010 CUP.

In a preferred embodiment, the invention provides for a Cucumber fruit of variety NUN 52010 CUP, or a part of a fruit of said varieties. The fruit can be in any stage of maturity, for example immature or mature. In another embodiment, the invention provides for a container comprising or consisting of a plurality of harvested Cucumber fruits or parts of fruits of said variety, or fruits of progeny thereof, or fruits of a derived variety. In a preferred embodiment, the fruit is seedless.

In another embodiment the plant, plant part or seed of NUN 52010 CUP is inside a container, For example, containers such as cans, boxes, crates, bags, cartons, Modified Atmosphere Packaging, films (e.g. biodegradable films), etc. comprising a plant or a part of a plant (fresh and/or processed) of NUN 52010 CUP or a seed of NUN 52010 CUP are also provided herein. In a preferred embodiment, the container comprises a plurality of seeds of NUN 52010 CUP, or a plurality of plant parts of NUN 52010 CUP.

The present invention further relates to a Cucumber variety, referred to as NUN 52010 CUP, which—when compared to its REFERENCE VARIETY Gershwin—has the following distinguishing characteristic: 1) Average fruit diameter at medial at harvest maturity; 2) Spine density type at edible maturity; 3) Type of stem end cross section at edible maturity; 4) Type of blossom end cross section at edible maturity; 5) Average leaf petiole length; 6) Average leaf length; 7) Average leaf width; 8) Average number of nodes form Cotyledon leaves to node bearing the first pistillate flower; and 9) Average leaf petiole diameter, where the characteristics are determined at the 5% significance level for plants grown under the same environmental conditions. Also encompassed by the present invention are parts of that plant.

In one embodiment a plant of NUN 52010 CUP or a progeny plant thereof, comprises all of the following morphological and/or physiological characteristics (i.e. average values of distinguishing characteristics, as indicated on the USDA Objective description of variety—Cucumber (unless indicated otherwise)): 1) Average fruit diameter at medial at harvest maturity; 2) Spine density type at edible maturity; 3) Type of stem end cross section at edible maturity; 4) Type of blossom end cross section at edible maturity; 5) Average leaf petiole length; 6) Average leaf length; 7) Average leaf width; 8) Average number of nodes form Cotyledon leaves to node bearing the first pistillate flower; and 9) Average leaf petiole diameter, where the characteristics are determined at the 5% significance level for plants grown under the same environmental conditions. An example of values for the distinguishing characteristics collected in a trial run according to UDSA requirements can be found in Table 1. A part of this plant is also provided.

NUN 52010 CUP may further exhibit at least one further trait selected from the group consisting of a) average petiole diameter, b) average tubercle density.

The invention further provides a Cucumber plant which does not differ from the plant of NUN 52010 CUP as determined at the 1%, 2%, 3%, 4% or 5% significance level when grown under the same environmental conditions. Thus the plants are measured in the same trial. Preferably, the trial is conducted as recommended by the USDA or UPOV. The invention also comprises a part of said plant The invention also provides a tissue or cell culture comprising cells of NUN 52010 CUP. Such a tissue culture can for example be grown on plates or in liquid culture, or be frozen for long term storage. The cells of NUN 52010 CUP used to start the culture can be selected from any plant part suitable for vegetative reproduction, or in a preferred embodiment can be selected from embryos, meristems, cotyledons, hypocotyl, pollen, leaves, anthers, roots, root tips, pistil, petiole, flower, fruit, seed, stem and stalks of NUN 52010 CUP. In another preferred embodiment, the tissue culture does not contain somaclonal variation or has reduced somaclonal variation. The skilled person is familiar with methods to reduce or prevent somaclonal variation, including regular reinitiation.

In one embodiment the invention provides a Cucumber plant regenerated from the tissue or cell culture of NUN 52010 CUP, wherein the regenerated plant is not significantly different from NUN 52010 CUP in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another embodiment, the invention provides a Cucumber plant regenerated from the tissue or cell culture of NUN 52010 CUP, wherein the plant has all of the physiological and morphological characteristics of said variety determined at the 5% significance level when grown under the same environmental conditions. In these cases, similarity or difference of a characteristic is determined by measuring the characteristics of a representative number of plants grown under the same environmental conditions, determining whether type/degree characteristics are the same or different and determining whether numerical characteristics are significantly different (determined at the 5% significance level).

A Cucumber according to the invention, such as NUN 52010 CUP, or its progeny, or a plant having all physiological and/or morphological characteristics but one, two or three which are different from those of NUN 52010 CUP, can also be reproduced using vegetative reproduction methods. Therefore, the invention provides for a method of producing a plant, or a part thereof, of variety NUN 52010 CUP, comprising vegetative propagation of said variety. Vegetative propagation comprises regenerating a whole plant from a plant part of variety NUN 52010 CUP (or from a progeny of said variety or from or a plant having all physiological and/or morphological characteristics of said variety but one, two or three different characteristics), such as a cutting, a cell culture or a tissue culture.

The invention also concerns methods of vegetatively propagating a part of the plant of the invention NUN 52010 CUP. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets. Therefore, the method also comprises regenerating a whole plant from said part of NUN 52010 CUP.

In a preferred embodiment, the part of the plant to be propagated is is a cutting, a cell culture or a tissue culture.

The invention also provides for a vegetatively propagated plant of variety NUN 52010 CUP (or from progeny of said variety or from or a plant having all but one, two or three physiological and/or morphological characteristics of NUN 52010 CUP) wherein the plant has all of the morphological and physiological characteristics of NUN 52010 CUP when the characteristics are determined at the 5% significance level for plants grown under the same conditions. In another embodiment, the propagated plant has all but one, two or three of the morphological and physiological characteristics of NUN 52010 CUP when the characteristics are determined at the 5% significance level for plants grown under the same conditions. A part of said propagated plant or said propagated plant with one, two or three differences is also included.

In an embodiment, the invention provides a method for producing a Cucumber plant part, preferably a fruit, comprising the steps of:
 a. Growing a plant of NUN 52010 CUP until it sets at least one fruit
 b. Collecting the fruit of step a)

Preferably, the fruit is collected at harvest maturity. In another embodiment, the fruit is collected when the seed is ripe. A plant of NUN 52010 CUP can be produced by seeding directly in the soil (e.g., field) or by germinating the seeds in controlled environment conditions (e.g., greenhouses) and optionally then transplanting the seedlings into the field. For example, the seed can be sown into prepared seed beds where they will remain for the entire production the crop. Alternatively, the Cucumber seed may be planted through a black plastic mulch. The dark plastic will absorb heat from the sun, warming the soil early. It will also help to conserve moisture during the growing season, controls weeds and makes harvesting easier and cleaner. Cucumber can also be grown entirely in greenhouses.

In still another aspect the invention provides a method of producing a Cucumber plant, comprising crossing a plant of Cucumber NUN 52010 CUP with a second Cucumber plant at least once, allowing seed to develop and optionally harvesting said progeny seed. The skilled person can select progeny from said crossing. Optionally, the progeny is crossed twice, thrice, or four, five, six or seven times, and allowed to set seed. In one embodiment of the invention, the first step in "crossing" comprises planting seeds of a first and a second parent Cucumber plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

In yet another aspect the invention provides a method of producing a plant, comprising selfing a plant of variety NUN 52010 CUP one or more times, and selecting a progeny plant from said selfing. In one aspect the progeny plant retains all the distinguishing characteristics of NUN 52010 CUP described above. In a different embodiment the progeny plant comprises all (or all but one, two or three) of the physiological and morphological characteristic of NUN 52010 CUP of Table 1, and/or Table 2. In a further embodiment the progeny plant comprises all physiological and morphological characteristic of NUN 52010 CUP when grown under the same environmental conditions.

In other aspects, the invention provides a progeny plant of variety NUN 52010 CUP such as a progeny plant obtained by further breeding that variety. Further breeding with the variety of the invention includes selfing that variety one or more times and/or cross-pollinating that variety with another Cucumber plant or variety one or more times. In particular, the invention provides for a progeny plant that retains all the essential morphological and physiological characteristics of NUN 52010 CUP or, in another embodiment, a progeny plant that retains all, or all but one, two or three, of the morphological and physiological characteristics of NUN 52010 CUP, optionally all or all but one, two or three of the characteristics as listed in Table 1 and/or 2, when grown under the same environmental conditions, determined at the 5% significance level for numerical characteristics. In a preferred embodiment, the progeny is a first generation progeny, i.e. the ovule or the pollen (or both) used in the crossing is an ovule or pollen of variety NUN 52010 CUP, i.e. the pollen comes from an anther of NUN 52010 CUP and the ovule comes from an ovary of NUN 52010 CUP. In another aspect, the invention provides for a vegetative reproduction of the variety and a plant having all, or all but 1, 2, or 3 of the physiological and morphological characteristics of NUN 52010 CUP (e.g. as listed in Table 1 and/or 2).

The invention also provides a method for collecting pollen of NUN 52010 CUP, comprising the steps of:
 a. Growing a plant of NUN 52010 CUP until at least one flower contains pollen
 b. Collecting the pollen of step a)

Preferably, the pollen is collected when it is mature or ripe. A suitable method for collecting pollen comprises collecting anthers or the part of the anther that contains pollen, for example by cutting it off. Pollen can be collected in containers. Optionally, collected pollen can be used to pollinate a Cucumber flower.

The morphological and/or physiological differences between two different individual plants of the invention (e.g. between NUN 52010 CUP and a progeny of NUN 52010 CUP) or between a plant of NUN 52010 CUP or progeny of said variety, or a plant having all, or all but 1, 2, or 3, of the physiological and morphological characteristics of NUN 52010 CUP (or all, or all but 1, 2, or 3 of the characteristics as listed in Table 1 and/or 2) and another known variety can easily be established by growing said variety next to each other or next to the other variety (in the same field, under the same environmental conditions), preferably in several locations which are suitable for said Cucumber cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby various characteristics, for example maturity, days from seeding to harvest, plant habit, plant attitude, leaf shape, leaf color, blistering, numbers of flowers per leaf axil, number of calyx lobes, number of petals, fruit group, immature fruit color, mature fruit color, pungency, flavor, fruit glossiness, fruit size, fruit shape, average number of fruits per plant, seed size, seed weight, anthocyanin level, disease resistance, insect resistance, can be measured and directly compared for species of Cucumber. Thus, the invention comprises Cucumber plant having one, two or three physiological and/or morphological characteristics which are different from those of the plant of NUN 52010 CUP and which otherwise has all the physiological and morphological characteristics of the plant of NUN 52010 CUP, when determined at the 5% significance level for plants grown under the same environmental conditions. In a preferred embodiment, the different characteristic is affected by a mutation, optionally induced mutation, or by transformation.

The morphological and physiological characteristics (and the distinguishing characteristics) of NUN 52010 CUP are provided in the Examples, in Table 1 and/or 2. Encompassed herein is also a plant obtainable from NUN 52010 CUP (e.g. by selfing and/or crossing and/or backcrossing with said variety and/or progeny of said variety) comprising all or all but one, two or three of the physiological and morphological characteristics of NUN 52010 CUP listed in Table 1 and/or 2 as determined at the 5% significance level for numerical characteristics or identical for non-numerical characteristics when grown under the same environmental conditions and/or comprising one or more (or all; or all except one, two or three) characteristics when grown under the same environmental conditions.

Also at-harvest and/or post-harvest characteristics of fruits can be compared, such as cold storage holding quality, post-harvest flesh firmness, and Brix can be measured using known methods. (Fruit) Flesh firmness can for example be measured using a penetrometer, e.g. by inserting a probe into the fruit flesh and determining the insertion force, or by other methods. Fruit flesh firmness can for example be measured using a "FT 327 Penetrometer", available from QA Supplies LLC, 1185 Pineridge Road, Norfolk, Va. 23502.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World Wide Web at rhs.org.uk/Plants/RHS-Publications/RHS-colour-charts).

In yet a further embodiment, the invention provides for a method of producing a new Cucumber plant. The method comprises crossing a plant of the invention i.e. NUN 52010 CUP, or a plant comprising all but 1, 2, or 3 of the morphological and physiological characteristics of said variety (as listed in Table 1 and/or 2), or a progeny plant thereof, either as male or as female parent, with a second Cucumber plant (or a wild relative of Cucumber) one or more times, and/or selfing a Cucumber plant according to the invention i.e. NUN 52010 CUP, or a progeny plant thereof, one or more times, and selecting progeny from said crossing and/or selfing. The second Cucumber plant may for example be a line or variety of the species *C. sativus* L., *Cucumis hystrix*, *Cucumis ritchiei* (syn. *Dicaelospermum ritchiei*) or *Cucumis maderaspatana* (syn. *Mukia maderaspatana*).

The invention provides for methods of producing plants which retain all the morphological and physiological characteristics of a plant of the invention i.e. NUN 52010 CUP. The invention provides also for methods of producing a plant comprising all but 1, 2, or 3 or more of the morphological and physiological characteristics of NUN 52010 CUP (e.g. as listed in Table 1 and/or 2), but which are still genetically closely related to said variety. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 52010 CUP if its DNA fingerprint is at least 80%, 90%, 95% or 98% identical to the fingerprint of NUN 52010 CUP. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Parvathaneni et al., J. Crop Sci. Biotech. 2011 (March) 14 (1): 39-43).

The invention also provides a plant and a variety obtained or selected by applying these methods on NUN 52010 CUP. Such a plant may be produced by crossing and/or selfing, or alternatively, a plant may simply be identified and selected amongst plants of said variety, or progeny of said variety, e.g. by identifying a variant within NUN 52010 CUP or within progeny of said variety (e.g. produced by selfing) which variant differs from NUN 52010 CUP in one, two or three of the morphological and/or physiological characteristics (e.g. in one, two or three distinguishing characteristics), e.g. those listed in Table 1 and/or 2 or others. In one embodiment the invention provides a Cucumber plant having a Jaccard's Similarity index with NUN 52010 CUP of at least 0.8, e.g. at least 0.85, 0.9, 0.95, 0.98 or even at least 0.99.

WO2013182646, which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant of the invention i.e. NUN 52010 CUP is a progeny of said variety, because the seed coat of the seed is a maternal tissue genetically identical to NUN 52010 CUP. In one embodiment, the present invention relates to a seed coat comprising maternal tissue of NUN 52010 CUP. In another embodiment the invention relates to a Cucumber seed comprising a maternal tissue of NUN 52010 CUP.

By crossing and/or selfing also (one or more) single traits may be introduced into the variety of the invention i.e. NUN 52010 CUP (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g. dominant or recessive) and one or more QTLs (quantitative trait loci) may be transferred into NUN 52010 CUP by breeding with said variety.

Alternatively, a single trait converted plant or single locus converted plant of NUN 52010 CUP may be produced by the following steps
  a. obtaining a cell or tissue culture of cells of NUN 52010 CUP;
  b. genetically transforming or mutating said cells;
  c. growing the cells into a plant; and
  d. optionally selecting a plant that contains the desired single locus conversion The skilled person is familiar with various techniques for genetically transforming a single locus in a plant cell, or mutating said cells.

Any pest or disease resistance genes may be introduced into a plant according to the invention, i.e. NUN 52010 CUP, progeny of said variety or into a plant comprising all but 1, 2, or 3 or more of the morphological and physiological characteristics of NUN 52010 CUP (e.g. as listed in Table 1). Resistance to one or more of the following diseases or pests is preferably introduced into plants of the invention: Angular Leaf Spot (*Pseudomonas lachrymans*), Anthracnose (Race 1), *Colletotrichum lagenaria*, Anthracnose (Race 2), Bacterial Wilt (*Erwinia tracheiphilus*), Cucumber Scab (Gummosis) (*Cladosporium cucumerinum*), Downy Mildew, Powdery Mildew (*Erysiphe chicoracearum*), Alternaria Leaf Blight (*Alternaria cucumerina*), Target Spot (*Corynespora cassiicola*), Cucumber Yellow Mottle Mosaic Virus (Cucumis Virus 1), Cucumber Green Mottle Mosaic Virus (Cucumis Virus 2), Cucumber Aucuba Mosaic Virus (Cucumis Virus 2A), Muskmelon Mosaic Virus, Watermelon Mosaic Virus, Papaya Ring Spot Virus, Zucchini Mosaic Virus, Cucumber Rust, Root Rot, Crown Blight, Verticillum Wilt, Sulphur Burn, *Fusarium oxysporum* f. sp. *cucumberis* (Fom) race 0, *Fusarium oxysporum* f. sp. *cucumberis* (Fom) race 1, *Fusarium oxysporum* f. sp. *cucumberis* (Fom) race 2, Fusarium Wilt R2, Root Knot (Nematode), Anthracnose, and Squash Mosaic.

Thus, invention also provides a method for developing a Cucumber plant in a Cucumber breeding program, using a Cucumber plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 52010 CUP or progeny of said variety, or a plant comprising all but 1, 2, or 3 or more of the morphological and physiological characteristics of NUN 52010 CUP (e.g. as listed in Table 1 and/or 2), with a different Cucumber plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Martin et al. 2008, Australian Journal of Crop Science 1(2): 43-46). For breeding methods in general see Principles of Plant Genetics and Breeding, 2007, George Acquaah, Blackwell Publishing, ISBN-13: 978-1-4051-3646-4.

The invention also provides a Cucumber plant comprising at least a first set of the chromosomes of Cucumber variety NUN 52010 CUP, a sample of seed of said variety will be deposited under Accession Number NCIMB 43415; optionally further comprising a single locus conversion or a mutation, wherein said plant has essentially all of the morphological and physiological characteristics of the plant comprising at least a first set of the chromosomes of said variety. In another embodiment, this single locus conversion confers a trait selected from the group consisting of yield, storage properties, color, male sterility, herbicide tolerance, insect resistance, pest resistance, disease resistance, environmental stress tolerance, modified carbohydrate metabolism and modified protein metabolism.

In one embodiment, a plant according to the invention, i.e. NUN 52010 CUP may also be mutated (by e.g. irradiation, chemical mutagenesis, heat treatment, etc.) and mutated seeds or plants may be selected in order to change one or more characteristics of said variety. Methods such as TILLING may be applied to Cucumber populations in order to identify mutants. Similarly, NUN 52010 CUP may be transformed and regenerated, whereby one or more chimeric genes are introduced into the variety or into a plant comprising all but 1, 2, 3, or more of the morphological and physiological characteristics (e.g. as listed in Table 1 and/or 2). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 52010 CUP, or progeny of said variety, by transforming said variety or progeny of said variety with a transgene that confers the desired trait, wherein the transformed plant retains all or all but one, two or three of the phenotypic and/or morphological and/or physiological characteristics of NUN 52010 CUP or the progeny of said variety and contains the desired trait.

The invention also provides a plant or a cell of a plant comprising a desired trait produced by mutating a plant of variety NUN 52010 CUP or a cell thereof and selecting a plant the desired trait, wherein the mutated plant retains all or all but one of the phenotypic and morphological characteristics of said variety, optionally as described for each variety in in Table 1 and/or 2, and contains the desired trait and wherein a representative sample of seed of variety NUN 52010 CUP will be deposited under Accession Number NCIMB 43415. In a further embodiment, the desired trait is selected from the group consisting of yield, compact Cucumber, fruit quality, male sterility, herbicide tolerance, insect resistance, pest resistance, disease resistance, Powdery mildew resistance without necrosis, environmental stress tolerance, modified carbohydrate metabolism, modified protein metabolism and ripening.

A suitable method for inducing mutation in NUN 52010 CUP comprises the steps of:
a. Exposing a seed, a plant or a plant part or a cell of NUN 52010 CUP to a mutagenic compound or to radiation, wherein a representative sample of seed of NUN 52010 CUP is deposited under Accession Number NCIMB 43415.
b. Selecting a seed, a plant or a plant part or a cell of NUN 52010 CUP having a mutation
c. Optionally growing and/or multiplying the seed, plant or plant part or cell of NUN 52010 CUP having the mutation.

The invention also provides a plant having one, two or three physiological and/or morphological characteristics which are different from those of NUN 52010 CUP and which otherwise has all the physiological and morphological characteristics of said variety, wherein a representative sample of seed of variety NUN 52010 CUP will be deposited under Accession Number NCIMB 43415. In particular variants which differ from NUN 52010 CUP in none, one, two or three of the characteristics mentioned in Table 1 and/or 2 are encompassed.

A part of a variety of the invention, i.e. NUN 52010 CUP (or of progeny of said varieties or of a plant having all physiological and/or morphological characteristics but one, two or three which are different from those of said variety) encompasses any cells, tissues, organs obtainable from the seedlings or plants, such as but not limited to: a Cucumber fruit or a part thereof, a cutting, hypocotyl, cotyledon, seed coat, pollen and the like. Such parts can be stored and/or processed further. Encompassed are therefore also food or feed products comprising a part of NUN 52010 CUP or a part of progeny of said varieties, or a part of a plant having all but one, two or three physiological and/or morphological characteristics of NUN 52010 CUP, comprising one or more of such parts, optionally processed (such as canned, chopped, cooked, roasted, in a sauce, in a sandwich, pasted, puréed or concentrated, juiced, frozen, dried, pickled, or powdered).

In one aspect a haploid plant and/or a doubled haploid plant of NUN 52010 CUP, or of a plant having all but one, two or three physiological and/or morphological characteristics of NUN 52010 CUP, or progeny of any of these, is encompassed herein. Haploid and doubled haploid (DH) plants can, for example, be produced by cell or tissue culture and chromosome doubling agents and regeneration into a whole plant. For DH production chromosome doubling may be induced using known methods, such as colchicine treatment or the like (Nikolova and Niemirowicz-Szczytt (1996)).

In yet another aspect haploid plants and/or doubled haploid plants derived from NUN 52010 CUP that, when combined, make a set of parents of NUN 52010 CUP are encompassed herein. Thus the haploid plant and/or the doubled haploid plant of NUN 52010 CUP can be used in a method for generating parental lines of NUN 52010 CUP.

Using methods known in the art like "reverse synthesis of breeding lines" or "reverse breeding", it is possible to produce parental lines for a hybrid plant such as NUN 52010 CUP; where normally the hybrid is produced from the parental lines. Thus, this method introduces a tool that was not available in traditional breeding: a skilled person can take any individual heterozygous plant (called a "phenotypically superior plant" in Example 2 of WO2014076249; NUN 52010 CUP is such a plant) and generate a combination of parental lines (reverse breeding parental lines) that, when crossed, produce the variety NUN 52010 CUP. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Wijnker et al., Nature Protocols Volume: 9, Pages: 761-772 (2014) DOI: doi:10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 52010 CUP) comprising the step of making doubled haploid cells from haploid cells from said plant or a seed of that plant; and optionally crossing these parental lines to produce and collect seeds. In another aspect, the invention relates to a combination of parental lines produced by this method. In still another aspect said combination of parental lines can be used to produce a seed or plant of NUN 52010 CUP when these parental lines are crossed. In still another aspect, the invention relates to a combination of parental lines from which a seed or plant having all physiological and/or morphological characteristics of NUN 52010 CUP (when the characteristics are determined at the 5% significance level for plants grown under the same conditions).

In another aspect, the invention comprises a method for making doubled haploid cells from haploid cells of NUN 52010 CUP according to various methods known to the skilled person. A suitable method is colchicine treatment (Nikolova and Niemirowicz-Szczytt (1996))

In another alternative aspect, the invention provides a method of introducing a single locus conversion or single trait conversion or a desired trait into NUN 52010 CUP comprising:
  a. obtain a combination of a parental lines of NUN 52010 CUP, optionally through reverse synthesis of breeding lines,
  b. introduce a single locus conversion in at least one of the parents of step a;
  c. crossing the converted parent with the other parent of step a to obtain seed of NUN 52010 CUP A combination of a male and a female parental line of NUN 52010 CUP can be generated by methods described herein, for example through reverse synthesis of breeding lines.

In an embodiment of the invention, Step b) of the above method—introduce a single locus conversion in at least one of the parents of step a—may be done through the following method:
  i. obtaining a cell or tissue culture of cells of the parental line of NUN 52010 CUP;
  ii. genetically transforming or mutating said cells;
  iii. growing the cells into a plant; and
  iv. optionally selecting plants that contain the single locus conversion, the single trait conversion or the desired trait.

In another embodiment of the invention, Step b) of the above method—introduce a single locus conversion in at least one of the parents of step a—may also be done through the following method:
  i. crossing the parental line of NUN 52010 CUP with a second Cucumber plant comprising the single locus conversion, the single trait conversion or the desired trait;
  ii. selecting F1 progeny plants that contain the single locus conversion, the single trait conversion or the desired trait;
  iii. crossing said selected progeny plants of step ii with the parental line of step i, to produce a backcross progeny plant;
  iv. selecting backcross progeny plants comprising the single locus conversion, the single trait conversion or the desired trait and otherwise all or all but one, two or three of the morphological and physiological characteristics the parental line of step i to produce selected backcross progeny plants; and
  v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions.

The invention further relates to plants obtained by this method.

The above method is provided, wherein the single locus conversion concerns a trait, wherein the trait is yield or pest resistance or disease resistance. In one embodiment the trait is disease resistance and the resistance is conferred to Angular Leaf Spot (*Pseudomonas lachrymans*), Anthracnose (Race 1), *Colletotrichum lagenaria*, Anthracnose (Race 2), Bacterial Wilt (*Erwinia tracheiphilus*), Cucumber Scab (Gummosis) (*Cladosporium cucumerinum*), Downy Mildew, Powdery Mildew (*Erysiphe chicoracearum*), Alternaria Leaf Blight (*Alternaria cucumerina*), Target Spot (*Corynespora cassiicola*), Cucumber Yellow Mottle Mosaic Virus (Cucumis Virus 1), Cucumber Green Mottle Mosaic Virus (Cucumis Virus 2), Cucumber Aucuba Mosaic Virus (Cucumis Virus 2A), Muskmelon Mosaic Virus, Watermelon Mosaic Virus, Papaya Ring Spot Virus, Zucchini Mosaic Virus, Cucumber Rust, Root Rot, Crown Blight, Verticillum Wilt, Sulphur Burn, *Fusarium oxysporum* f. sp. *cucumberis* (Fom) race 0, *Fusarium oxysporum* f. sp. *cucumberis* (Fom) race 1, *Fusarium oxysporum* f. sp. *cucumberis* (Fom) race 2, Fusarium Wilt R2, Root Knot (Nematode), Anthracnose, and Squash Mosaic or Powdery mildew resistance without necrosis.

Thus, the invention also provides a combination of parental lines which, when crossed, produce a seed or plant having all physiological and/or morphological characteristics of NUN 52010 CUP but one, two or three which are different (when grown under the same environmental conditions), as well as a seed or plant having all physiological and/or morphological characteristics of NUN 52010 CUP but one, two or three which are different (when the characteristics are determined at the 5% significance level for plants grown under the same conditions).

Also provided is a plant part obtainable from variety NUN 52010 CUP or from progeny of said variety or from a plant having all but one, two or three physiological and/or morphological characteristics which are different from those of NUN 52010 CUP, or from a vegetatively propagated plant of NUN 52010 CUP (or from its progeny or from a plant having all or all but one, two or three physiological and/or morphological characteristics which are different from those of NUN 52010 CUP), being selected from the group consisting of a fruit, a harvested fruit, a part of a fruit, a seedless fruit, a leaf, a part of a leaf, pollen, an ovule, a cell, a petiole, a shoot or a part thereof, a stem or a part thereof, a root or a part thereof, a root tip, a cutting, a seed, a part of a seed, seed-coat or another maternal tissue which is part of a seed grown on NUN 52010 CUP, or hypocotyl, cotyledon, a scion, a stock, a rootstock, a pistil, an anther, and a flower or a part thereof.

In still yet another aspect, the invention provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a Cucumber fruit or part thereof and/or an extract from a fruit or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Marketable Cucumber fruits are generally sorted by size and quality after harvest. Alternatively the Cucumber fruits can be sorted by expected shelf life, pH or Brix.

Cucumbers may also be grown for use as rootstocks (stocks) or scions (cions). Typically, different types of Cucumbers are grafted to enhance disease resistance, which is usually conferred by the rootstock, while retaining the horticultural qualities usually conferred by the scion. It is not uncommon for grafting to occur between cultivated Cucumber varieties and related Cucumber species. Methods of grafting and vegetative propagation are well-known in the art.

So in one aspect the invention relates to a plant comprising a rootstock or scion of NUN 52010 CUP.

All documents (e.g., patent publications) are herein incorporated by reference in their entirety.

CITED REFERENCES

Acquaah, Principles of Plant Genetics and Breeding, 2007, Blackwell Publishing, ISBN-13: 978-1-4051-3646-4
Colijn-Hooymans (1994), Plant Cell, Tissue and Organ Culture 39: 211-217
Martin et al. 2008, Australian Journal of Crop Science 1(2): 43-46
Nikolova V, Niemirowicz-Szczytt K (1996) Acta Soc Bot Pol 65:311-317
Parvathaneni et al., J. Crop Sci. Biotech. 2011 (March) 14 (1): 39~43.
Pisanu et al. ISHS 2004, Acta Hort. 660
Sang-Gu et al. (1988), Plant Cell, Tissue and Organ Culture 12: 67-74
Sarreb et al. (2002), Plant Cell Tissue, Organ Culture 71: 231-235
Vos et al. 1995, Nucleic Acid Research 23: 4407-4414
Wijnker et al., Nature Protocols Volume: 9, Pages: 761-772 (2014) DOI: 10.1038/nprot.2014.049
U.S. Pat. No. 4,822,949
U.S. Pat. No. 5,349,128
U.S. Pat. No. 5,492,827
U.S. Pat. No. 6,084,152
U.S. Pat. No. 6,765,130
WO2013182646
WO2014076249
WO2016207432
WO2016120438
http://www.ams.usda.gov/AMSv1.0/getfile?dDocName=STELDEV3002687
http://www.ams.usda.gov/AMSv1.0/getfile?dDocName=STELDEV3002687
http://www.upov.int/en/publications/tg-rom/tg061/tg_61_7.pdf

EXAMPLES

Development of NUN 52010 CUP

The hybrid NUN 52010 CUP was developed from a male and female proprietary inbred line of Nunhems. The female and male parents were crossed to produce hybrid (F1) seeds of NUN 52010 CUP The seeds of NUN 52010 CUP can be grown to produce hybrid plants and parts thereof (e.g. Cucumber fruit). The hybrid NUN 52010 CUP can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that NUN 52010 CUP is uniform and stable.

DEPOSIT INFORMATION

A total of 2500 seeds of the hybrid variety NUN 52010 CUP will be deposited according to the Budapest Treaty by Nunhems B.V. on May 3, 2019, at the NCIMB Ltd., Ferguson Building, Craibstone Estate, Bucksburn, Aberdeen AB21 9YA, United Kingdom (NCIMB). The deposit will be assigned NCIMB number 43415. A deposit of NUN 52010 CUP and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 52010 CUP is referred to as Reference Variety, a variety from Rijk Zwaan with the commercial name Gershwin. In Table 1 a comparison between NUN 52010 CUP and the Reference Variety will be shown based on a trial in the USA during the trial season 2017. Trial location: Acampo, Calif., USA (N38.192873 W121.232637), Seeding date: 28 Jun. 2017.

A trial of 40 plants of each variety, from which at least 15 plants or plant parts were randomly selected, will be used to measure characteristics. For numerical characteristics averages will be calculated. For non-numerical characteristics the type/degree will be determined. In Table 1 the USDA descriptors of NUN 52010 CUP (this application) and the Reference Variety (commercial variety) are listed, which will be measured in the trial to be performed.

In accordance with one aspect of the present invention, there is provided a plant having the physiological and morphological characteristics of NUN 52010 CUP as will be presented in Table 1.

TABLE 1

Objective description of varieties NUN 52010 CUP and Reference Variety

| USDA descriptor | Application Variety NUN 52010 CUP | Reference Variety Gershwin |
|---|---|---|
| 1. TYPE | | |
| Predominate Usage (1 = slicing; 2 = pickling) | 2 | 2 |
| Predominate Culture (1 = outdoor; 2 = indoor) | 1 | 1 |
| Area of best adaptation (USA) (1 = north; 2 = south; 3 = most areas) | 3 | 3 |
| 2. MATURITY | | |
| Days From Seeding To Market | 54 | 54 |
| 3. PLANT | | |
| Habit (1 = bush; 2 = semi-bush; 3 = vine) | 3 | 3 |
| Growth (1 = determinate; 2 = indeterminate; 3 = other) | 3 semi-determinate | 3 semi-determinate |
| Sex (1 = Andromonoecious, 2 = Monoecious, 3 = Primarily Gynoecious, 4 = 100% Gynoecious | 4 | 4 |
| Flower color (1 = yellow; 2 = orange; 3 = green; 4 = other) (RHS color chart value) | 1 (RHS 13A) | 1 (RHS 13B) |
| 4. MAIN STEM | | |
| Length in cm | 88.38 | 86.16 |
| Number of nodes from cotyledon leaves to node bearing the first pistillate flower | 2.53 | 3.4 |
| Intermode length in cm | 3.38 | 3.26 |
| Stem form (1 = groved, ridged; 2 = smooth, round) | 1 | 1 |
| 5. LEAF (Mature blade of 3$^{rd}$ leaf) | | |
| Length in mm | 87.41 | 109.04 |
| Width in mm | 120.93 | 139.47 |
| Petiole length in cm | 16.8 | 13.9 |
| 6. FRUIT AT EDIBLE MATURITY | | |
| Length in cm | 12.53 | 12.76 |
| Diameter at medial in cm | 4.12 | 3.88 |
| Weight in g | 150.9 | 135.06 |
| Skin color (1 = not mottled; 2 = mottled or speckled with yellow) | 2 | 2 |
| Yellowish blossomed end stripes (1 = absent; 2 = extend less than ⅓ of fruit length; 3 = extend more than ⅓ of fruit length) | 2 | 2 |
| Predominant color at stem end (1 = white; 2 = light green; 3 = medium green; 4 = dark green) (RHS color chart value) | 4 (RHS 137A) | 4 (RHS NN137A) |

TABLE 1-continued

Objective description of varieties NUN 52010 CUP and Reference Variety

| USDA descriptor | Application Variety NUN 52010 CUP | Reference Variety Gershwin |
|---|---|---|
| Predominant color at blossom end (1 = white; 2 = light green; 3 = medium green; 4 = dark green) (RHS color chart value) | 2 (RHS 145C) | 2 (RHS 144C) |
| Fruit neck shape (1 = not necked; 2 = necked) | 1 | 1 |
| Fruit tapering (1 = both ends tapered; 4 = ends blunt or rounded) | 4 | 4 |
| Stem end cross section (1 = circular; 2 = triangular; 3 = square) | 2 | 1 |
| Medial cross section (1 = circular; 2 = triangular; 3 = square) | 2 | 2 |
| Blossom end cross section (1 = circular; 2 = triangular; 3 = square) | 2 | 1 |
| Skin Thickness (1 = thick; 2 = thin) | 1 | 1 |
| Skin Ribs (1 = not ribbed; 2 = ribbed) | 1 | 1 |
| Skin toughness (1 = tough; 2 = tender) | 1 | 1 |
| Skin luster (1 = dull; 2 = glossy) | 1 | 1 |
| Spine color (1 = white; 2 = black) | 1 | 1 |
| Spine quality (1 = coarse; 2 = fine) | 1 | 1 |
| Spine density (1 = few; 2 = many) | 1 | 2 |
| Tubercles (warts) (1 = few, obscure; 2 = many, obscure; 3 = few, prominent; 4 = many, prominent) | 1 | 1 |
| Flavor (1 = Bitterfree; 2 = Bitter) | n.r. | n.r. |
| 7. FRUIT AT MATURE STAGE (harvest maturity) | | |
| Length (cm) | 15.79 | 16.0 |
| Diameter at medial in cm | 5.57 | 5.98 |
| Color (1 = white; 2 = cream; 3 = yellow; 4 = orange; 5 = brown; 6 = red) (RHS color chart value) | 3 (RHS 10B) | 3 (RHS 9C) |
| Color pattern (1 = not striped; 2 = striped) | 1 | 1 |
| Surface (1 = smooth; 2 = rough) | 1 | 1 |
| Netting (1 = slight or none; 2 = heavy) | 1 | 1 |
| Fruit set (1 = parthenocarpically; 2 = normally with seeds) | 1 | 1 |
| 8. SEEDS | | |
| No. per Fruit | NA | n.r. |
| Gram per 1,000 | NA | n.r. |

TABLE 2

| Non - USDA descriptor | Application Variety NUN 52010 CUP | Reference Variety Gershwin |
|---|---|---|
| Petiole diameter (leaf) (mm) | 3.83 | 4.88 |
| Tubercle density (per 2 cm$^2$) | 7.4 | 6.9 |
| Fruit weight at harvest maturity (gram) | 324.5 | 358.3 |

Table 1 and 2 contain typical values. Values may vary due to environment. Other values that are substantially equivalent are also within the scope of the invention. N.A.=not applicable; n.r.=not recorded.

What is claimed is:

1. A plant, plant part or seed of cucumber variety NUN 52010 CUP, wherein a representative sample of seed of said cucumber variety is deposited under Accession Number NCIMB 43415.

2. The plant part of claim 1, wherein the plant part is a leaf, pollen, an ovule, a fruit, a parthenocarpic fruit, a scion, a root, a rootstock, cutting, a flower or a cell.

3. A seed that produces the plant of claim 1.

4. A seed grown on the plant of claim 1, wherein a plant grown from said seed does not differ from the plant of claim 1 when the characteristics are determined at the 5% significance level when grown under the same environmental conditions.

5. A cucumber plant or a part thereof derived from the plant of claim 1 which does not differ from the plant of claim 1 in any of the distinguishing characteristics of Tables 1 and 2, when the characteristics are determined at the 5% significance level for plants grown under the same environmental conditions, wherein a representative sample of seed of said cucumber variety NUN 52010 CUP is deposited under Accession Number NCIMB 43415.

6. A cucumber plant or a part thereof derived from the plant of claim 1 which does not differ from the plant of claim 1, when the characteristics are determined at the 5% significance level when grown under the same environmental conditions, wherein a representative sample of seed of said cucumber variety NUN 52010 CUP is deposited under Accession Number NCIMB 43415.

7. A tissue or cell culture comprising cells of the plant of claim 1.

8. The tissue or cell culture according to claim 7, comprising cells or protoplasts derived from a plant part, wherein the plant is an embryo, a meristem, a cotyledon, a hypocotyl, pollen, a leaf, an anther, a root, a root tip, a pistil, a petiole, a flower, a fruit, a seed, a stem, or a stalk.

9. A cucumber plant regenerated from the tissue or cell culture of claim 7, wherein the plant has all of the physiological and morphological characteristics of the plant of cucumber variety NUN 52010 CUP, when the characteristics are determined at the 5% significance level for plants grown under the same environmental conditions, and wherein a representative sample of seed of cucumber variety NUN 52010 CUP is deposited under Accession Number NCIMB 43415.

10. A method of producing the plant of claim 1 or a part thereof, said method comprising vegetative propagation of at least a part of the plant of cucumber variety NUN 52010 CUP, wherein a representative sample of seed of said cucumber variety is deposited under Accession Number NCIMB 43415.

11. The method of claim 10, wherein said vegetative propagation comprises regenerating a whole plant from said part of the plant of cucumber variety NUN 52010 CUP, wherein a representative sample of seed of said cucumber variety is deposited under Accession Number NCIMB 43415.

12. The method of claim 10, wherein said part is a cutting, a cell culture or a tissue culture.

13. A vegetative propagated plant of claim 1 or a part thereof, wherein the vegetative propagated plant has all of the physiological and morphological characteristics of the plant of cucumber variety NUN 52010 CUP, when the characteristics are determined at the 5% significance level for plants grown under the same environmental conditions, and wherein a representative sample of seed of cucumber variety NUN 52010 CUP is deposited under Accession Number NCIMB 43415.

14. A method of producing a cucumber plant, comprising crossing the plant of claim 1 with a second cucumber plant at least once, and selecting a progeny cucumber plant from said crossing and optionally allowing the progeny to form seed.

15. A first generation progeny plant of the plant of claim 1 obtained by selfing or cross-pollinating the plant of claim 1 with another cucumber plant, wherein said progeny has all of the physiological and morphological characteristics of the plant of cucumber variety NUN 52010 CUP, when the characteristics are determined at the 5% significance level for plants grown under the same environmental conditions, and wherein a representative sample of seed of said cucumber variety is deposited under Accession Number NCIMB 43415.

16. A cucumber plant derived from the plant of claim 1 having one physiological or morphological characteristic which is different from those of the plant of claim 1, and which otherwise has all the physiological and morphological characteristics of the plant of claim 1, when the characteristics are determined at the 5% significance level for plants grown under the same environmental conditions, wherein a representative sample of seed of said cucumber variety NUN 52010 CUP is deposited under Accession Number NCIMB 43415.

17. The plant of claim 1, further comprising a single locus conversion, wherein said plant has all of the morphological and physiological characteristics of the plant of cucumber variety NUN 52010 CUP, wherein a representative sample of seed of said cucumber variety is deposited under Accession Number NCIMB 43415, when said characteristics are determined at the 5% significance level for plants grown under the same environmental conditions, optionally wherein the single locus conversion confers a trait of male sterility, herbicide tolerance, insect resistance, pest resistance, disease resistance, environmental stress tolerance, modified carbohydrate metabolism or modified protein metabolism.

18. A method of producing double haploids of the plant of claim 1 comprising making doubled haploid cells from haploid cells from the plant or seed of cucumber variety NUN 52010 CUP, wherein a representative sample of seed of cucumber variety NUN 52010 CUP is deposited under Accession Number NCIMB 43415.

19. A plant comprising the scion or rootstock of claim 2.

20. A container comprising the plant, the plant part or the seed of claim 1.

21. A food, a feed product or a processed product comprising the plant part of claim 2, wherein the plant part is a fruit or a part thereof.

22. A method of producing a cucumber fruit, comprising:
  a. growing the plant of claim 1 until it sets at least one fruit; and
  b. collecting at least one fruit.

23. A method of collecting pollen of cucumber variety NUN 52010 CUP comprising:
  a. growing the plant of claim 1 until at least one flower contains pollen; and
  b. collecting the pollen.

24. A method of producing a cucumber plant with a desired trait, comprising mutating a cucumber plant of variety NUN 52010 CUP and selecting a mutated plant with a desired trait, wherein the mutated plant retains all of the physiological and morphological characteristics of cucumber variety NUN 52010 CUP, when the characteristics are determined at the 5% significance level for plants grown under the same environmental conditions, and wherein a representative sample of seed of said cucumber variety has been deposited under Accession Number NCIMB 43415, and wherein the desired trait is male sterility, herbicide tolerance, pest resistance, environmental resistance, modified carbohydrate metabolism, modified protein metabolism or ripening.

\* \* \* \* \*